(12) United States Patent
Bruckheimer et al.

(10) Patent No.: US 7,211,107 B2
(45) Date of Patent: May 1, 2007

(54) INTRAVASCULAR PLATFORMS AND ASSOCIATED DEVICES

(75) Inventors: Elchanan Bruckheimer, Zichron Yaakov (IL); Simon Brueckheimer, London (GB); Issack Tavori, Herzlia (IL); Gil Naor, Ramot Hashavim (IL); Danny Kinarty, Haifa (IL)

(73) Assignee: Rafael Medical Technologies, Inc., Dover, DE (US)

( * ) Notice: Subject to any disclaimer, the term of this patent is extended or adjusted under 35 U.S.C. 154(b) by 142 days.

(21) Appl. No.: 10/476,859

(22) PCT Filed: May 7, 2002

(86) PCT No.: PCT/IL02/00358

§ 371 (c)(1),
(2), (4) Date: Nov. 6, 2003

(87) PCT Pub. No.: WO02/089869

PCT Pub. Date: Nov. 14, 2002

(65) Prior Publication Data

US 2004/0133269 A1    Jul. 8, 2004

(30) Foreign Application Priority Data

May 7, 2001    (IL) .................................. 143007

(51) Int. Cl.
*A61F 2/06* (2006.01)
*A61M 29/00* (2006.01)
(52) U.S. Cl. ...................... 623/1.36; 606/200; 606/198
(58) Field of Classification Search ............... 623/1.36; 606/200, 198, 199, 108, 194
See application file for complete search history.

(56) References Cited

U.S. PATENT DOCUMENTS

| | | | | |
|---|---|---|---|---|
| 3,952,747 A * | 4/1976 | Kimmell, Jr. | ............... | 606/195 |
| 4,727,873 A * | 3/1988 | Mobin-Uddin | ............... | 606/200 |
| 5,466,242 A * | 11/1995 | Mori | ........................... | 606/198 |
| 5,554,181 A * | 9/1996 | Das | ........................... | 623/1.12 |
| 5,733,294 A * | 3/1998 | Forber et al. | ............... | 606/151 |
| 5,957,949 A * | 9/1999 | Leonhardt et al. | ......... | 623/1.24 |
| 5,980,554 A * | 11/1999 | Lenker et al. | ............... | 606/198 |
| 6,064,428 A * | 5/2000 | Trosino et al. | ............... | 348/128 |
| 6,251,122 B1 * | 6/2001 | Tsukernik | .................... | 606/200 |
| 6,258,114 B1 * | 7/2001 | Konya et al. | ............... | 606/198 |
| 6,299,637 B1 * | 10/2001 | Shaolian et al. | ........... | 623/1.24 |
| 6,440,164 B1 * | 8/2002 | DiMatteo et al. | ........... | 623/1.24 |
| 6,482,222 B1 * | 11/2002 | Bruckheimer et al. | ...... | 606/200 |
| 6,494,909 B2 * | 12/2002 | Greenhalgh | ............... | 623/1.24 |
| 6,508,833 B2 * | 1/2003 | Pavcnik et al. | ............. | 623/1.15 |
| 6,613,074 B1 * | 9/2003 | Mitelberg et al. | .......... | 623/1.11 |
| 6,793,665 B2 * | 9/2004 | McGuckin, Jr. et al. | .... | 606/200 |
| 2003/0208226 A1 * | 11/2003 | Bruckheimer et al. | ...... | 606/200 |
| 2004/0186512 A1 * | 9/2004 | Bruckheimer et al. | ...... | 606/200 |

FOREIGN PATENT DOCUMENTS

| | | |
|---|---|---|
| WO | WO01/19231 | 3/2001 |
| WO | WO02/04040 | 1/2002 |

\* cited by examiner

*Primary Examiner*—Alvin J. Stewart
(74) *Attorney, Agent, or Firm*—Mark M. Friedman

(57) ABSTRACT

An intravascular platform for supporting an intravascular device includes two loops of wire each configured to assume a shape lying generally on a virtual cylinder of given diameter. The two loops are interconnected by at least one connecting wire which maintains the loops axially spaced from each other. Also disclosed are axially-extended loop forms, and associated intravascular devices.

20 Claims, 12 Drawing Sheets

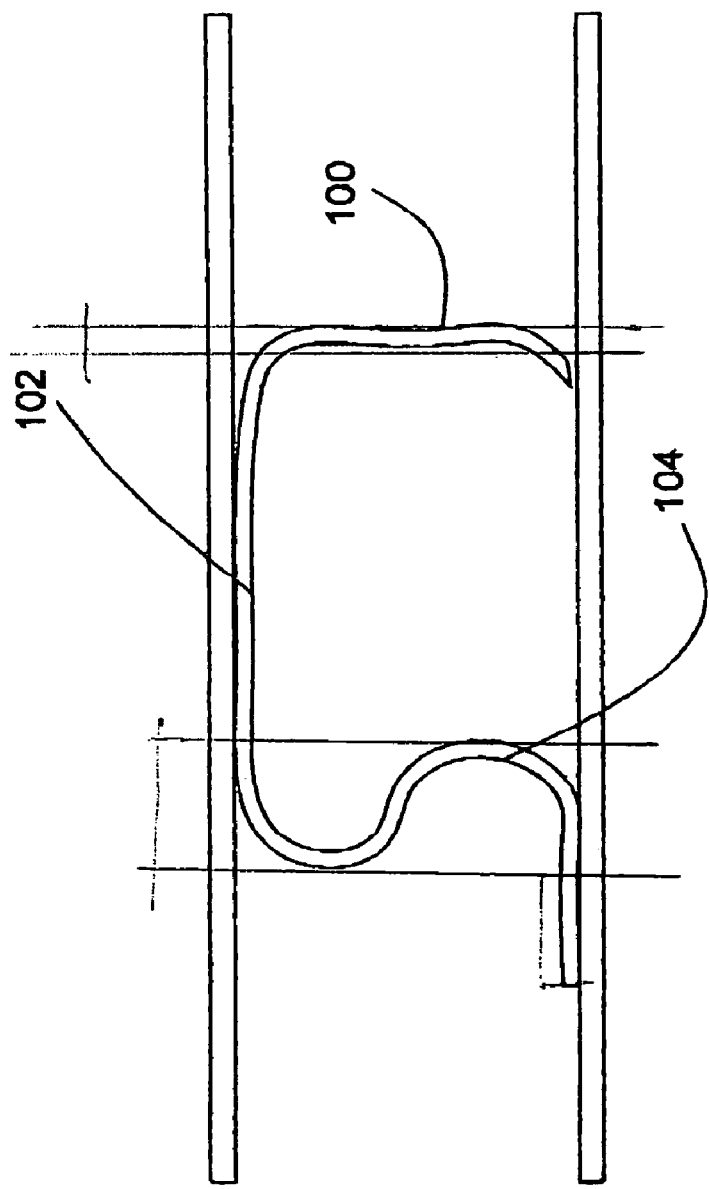

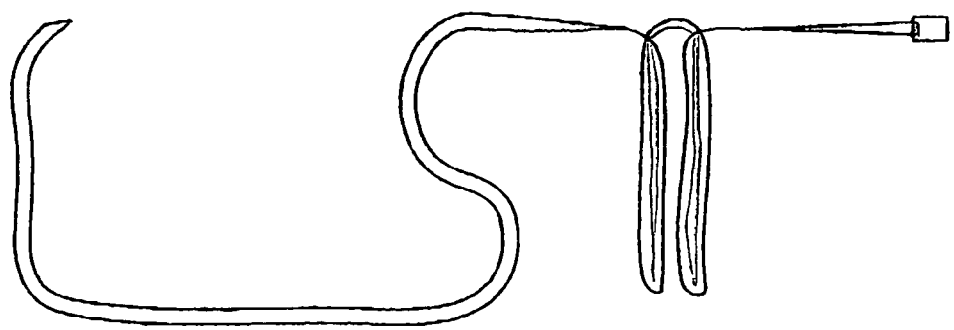
FIG. 6
FIG. 7
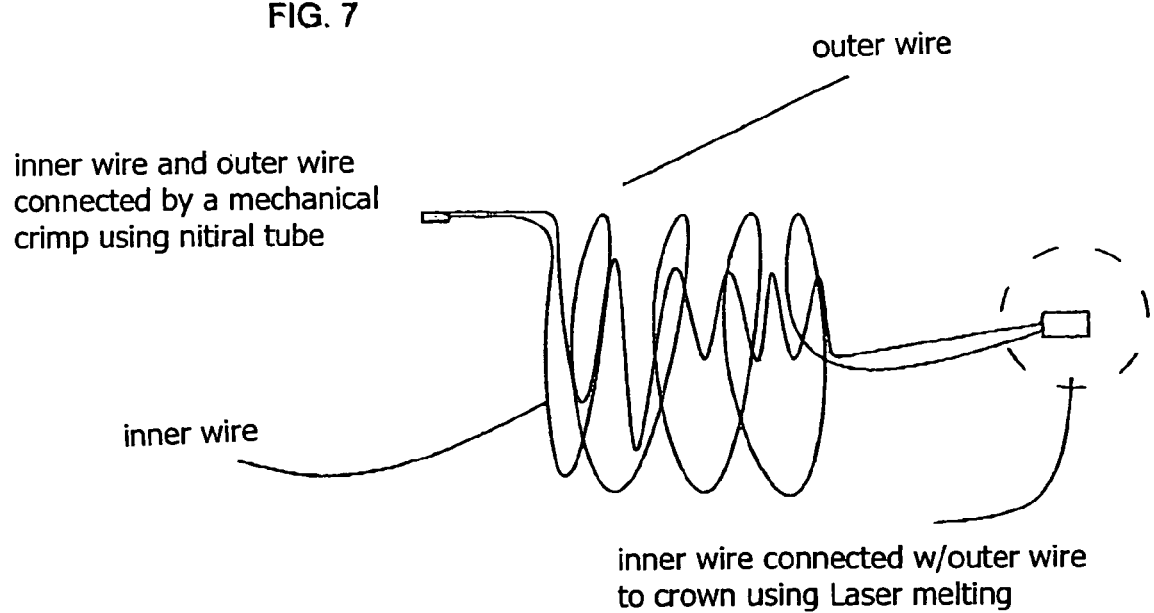
inner wire and outer wire connected by a mechanical crimp using nitiral tube
outer wire
inner wire
inner wire connected w/outer wire to crown using Laser melting FIG. 8
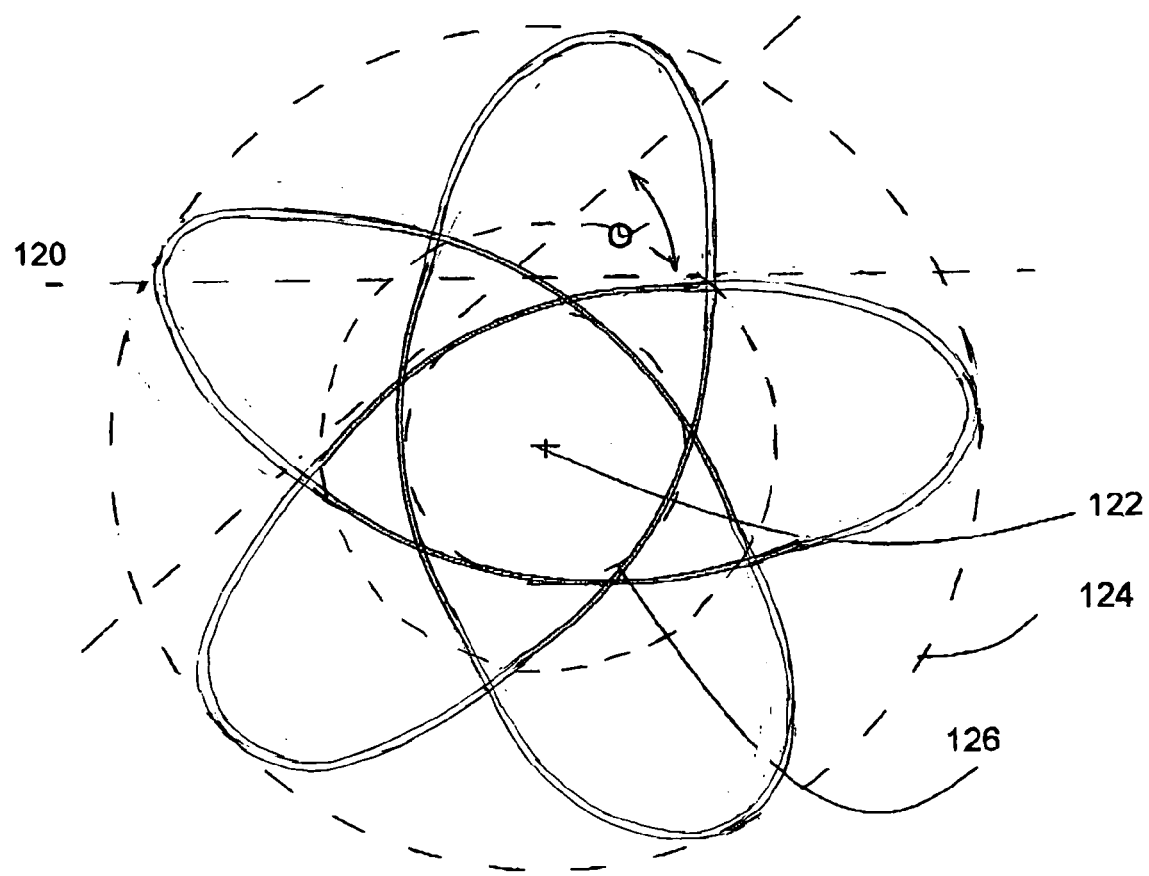
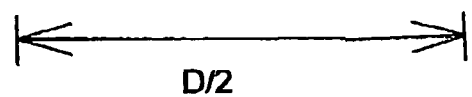
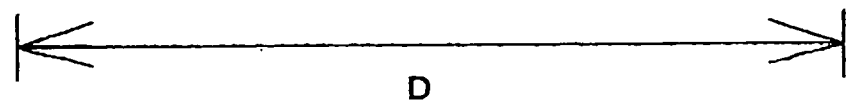

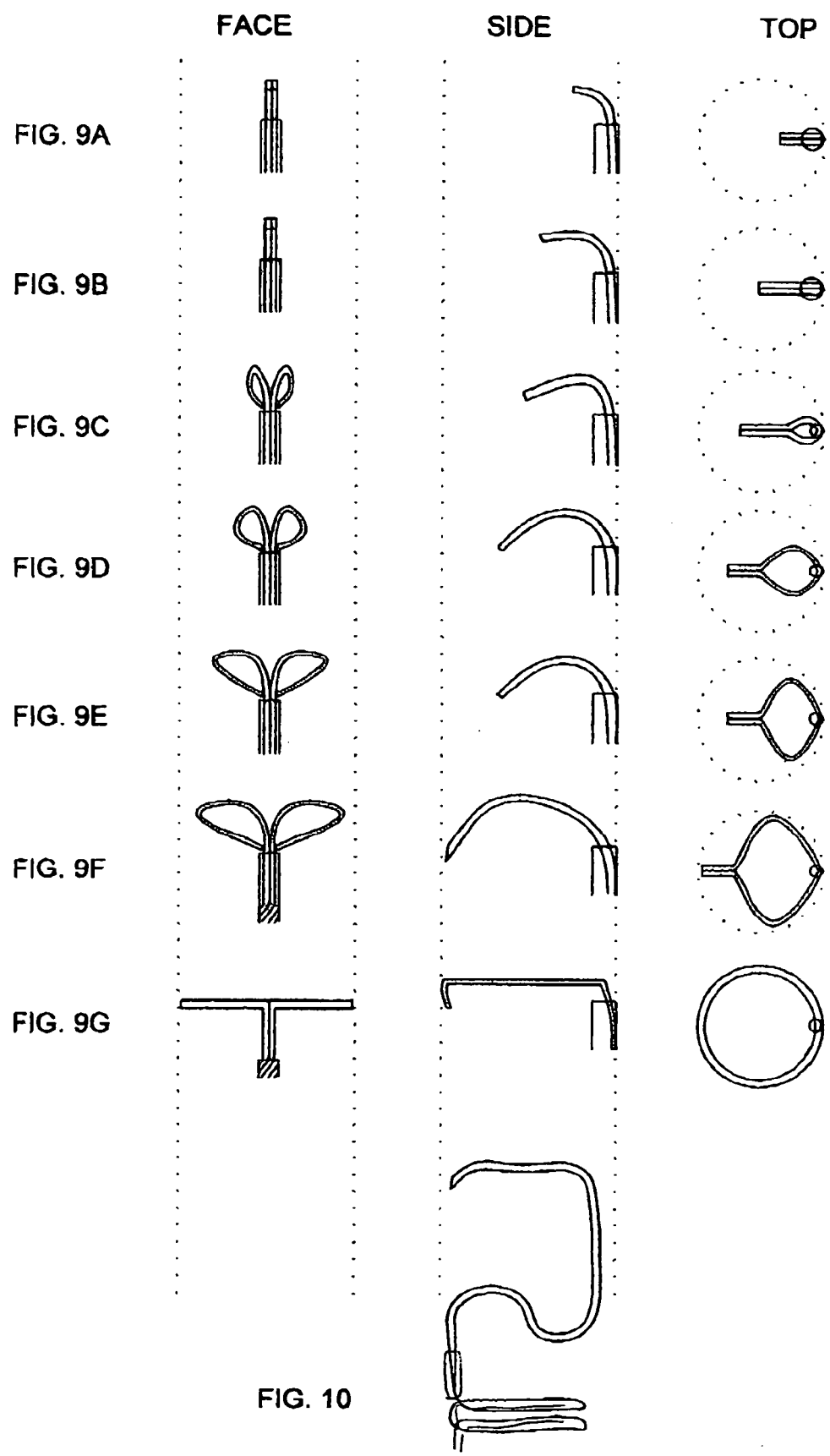

FIG. 11
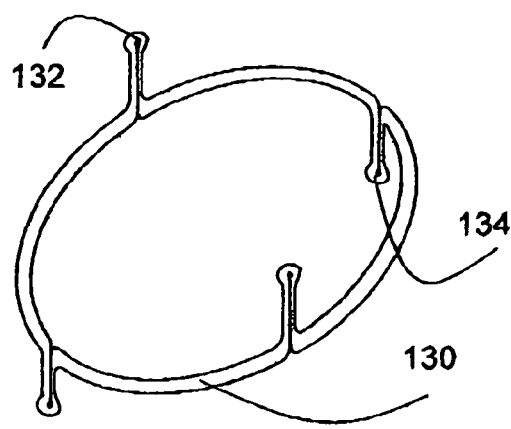
FIG. 12
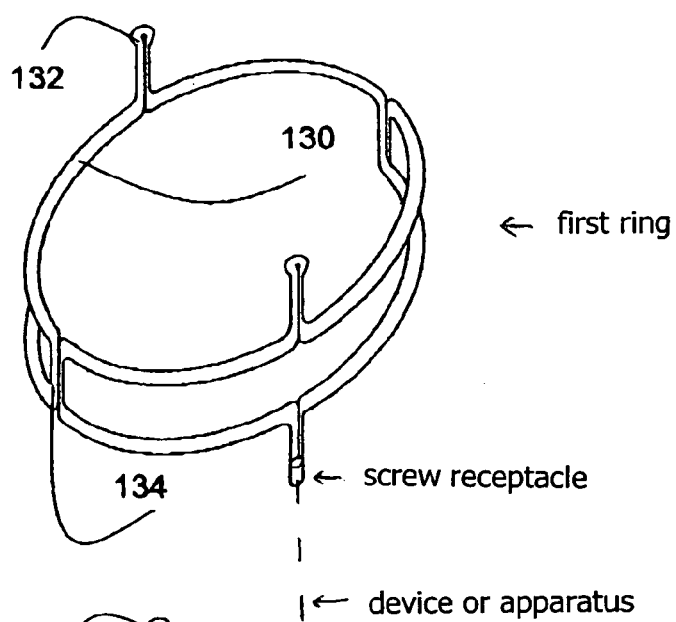
← first ring
← screw receptacle
← device or apparatus
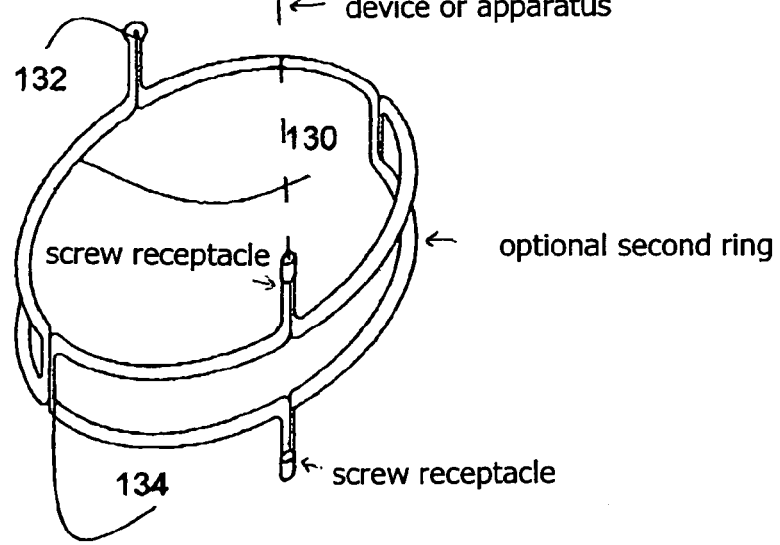
← optional second ring
← screw receptacle
← screw receptacle

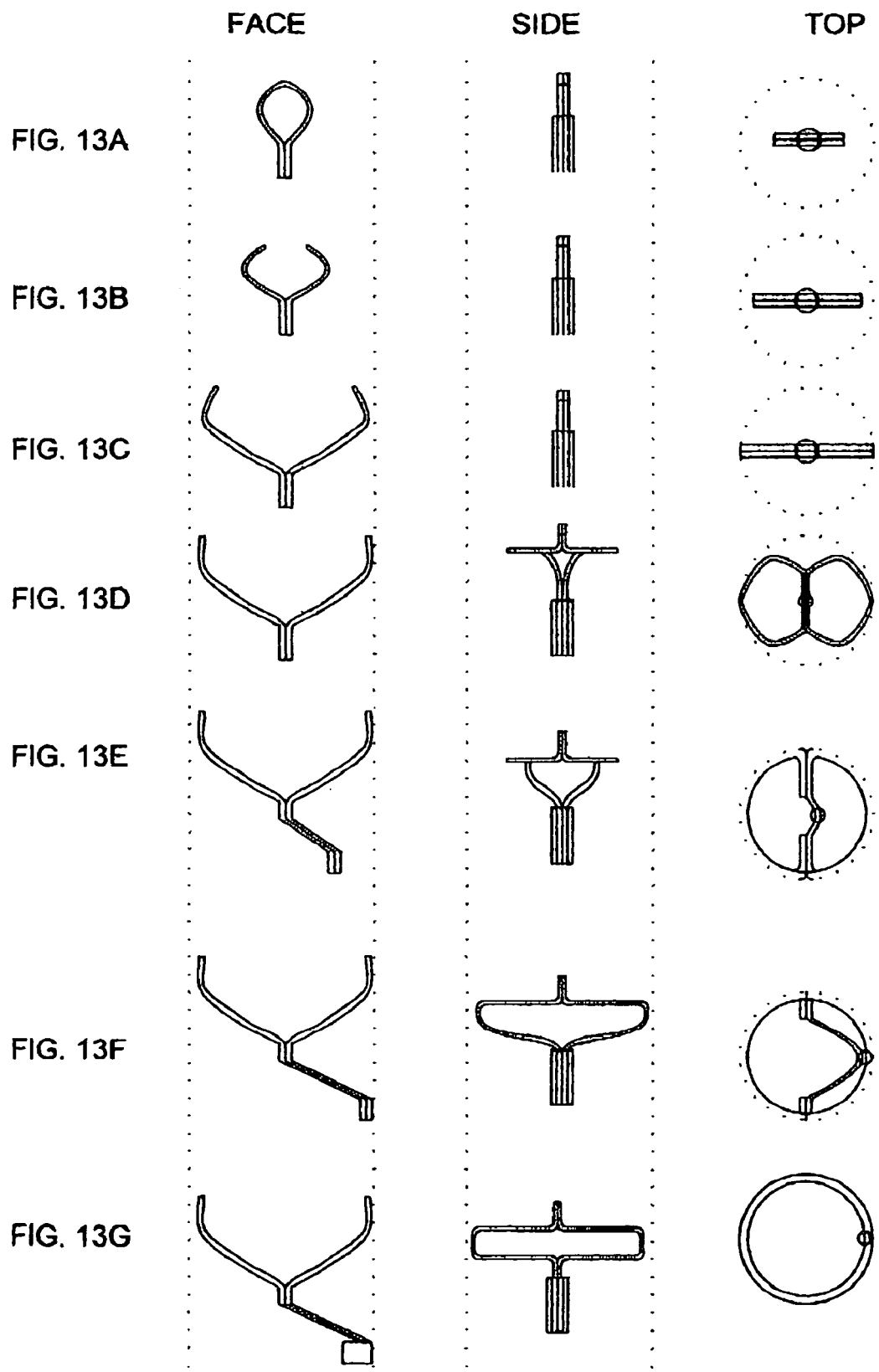

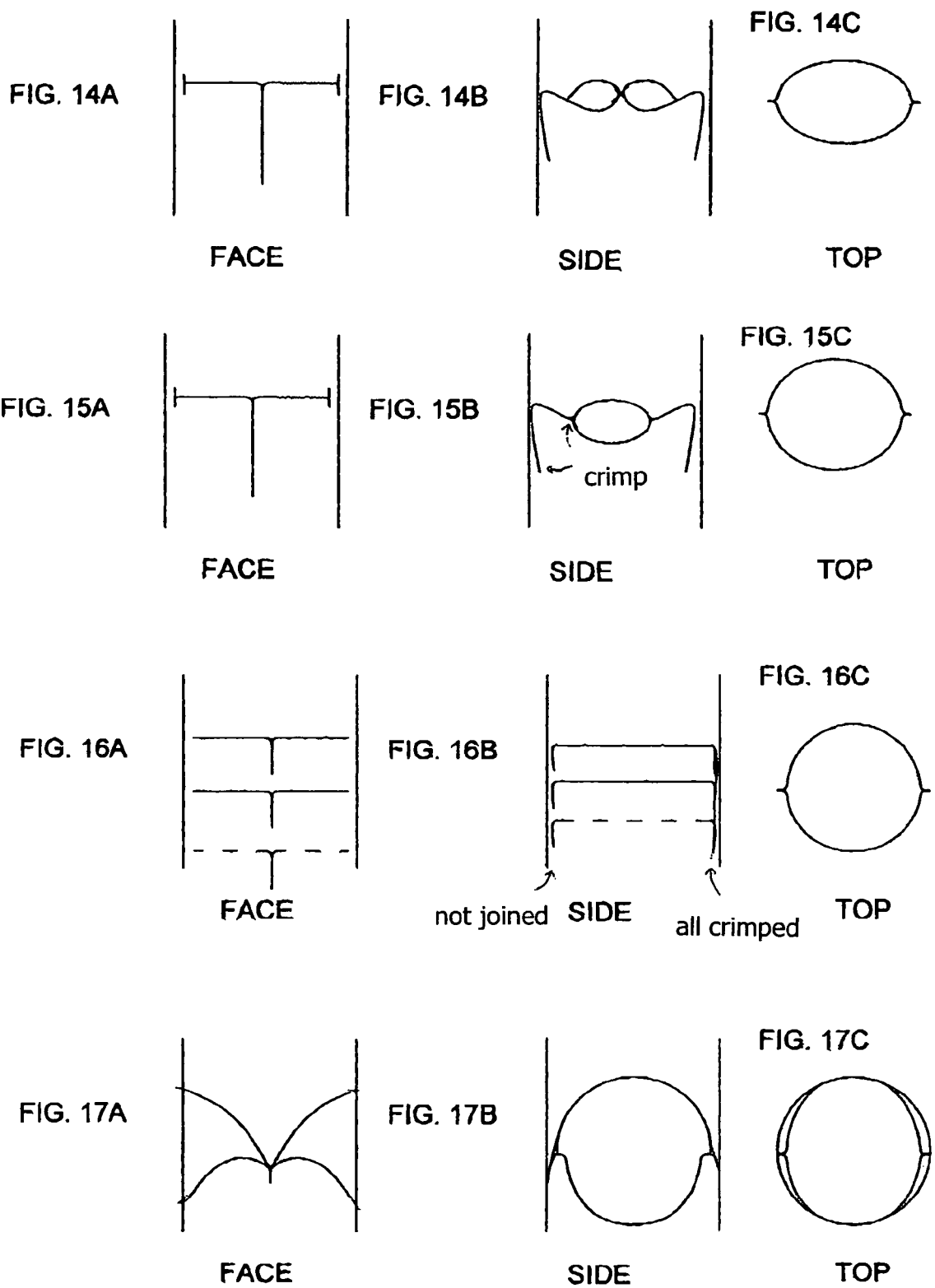

INTRAVASCULAR PLATFORMS AND ASSOCIATED DEVICES

FIELD AND BACKGROUND OF THE INVENTION

The present invention relates to intravascular devices and, in particular it concerns platforms for supporting intravascular devices within vessels, and devices for use with such platforms.

Trauma, injury, and/or disease may require medical intervention to rectify damage and/or monitor progress or the provision of prolonged drug therapy or other systemic means by use of intravascular devices or apparatus. It is beneficial to the patient to be able to introduce such devices or apparatus with minimal operative procedure, and where necessary their complete removal with similar minimal operative procedure.

The present invention provides a support system for a wide range of devices or apparatus that need to be held in a particular position inside a vessel of the body. With the exception of certain features of a preferred intravascular filter device, a detailed description of the function of any thus supported device or apparatus is not addressed in this text.

PCT Patent Publication No. WO01/19231 discloses a ring platform for deployment using minimal invasive surgical techniques to support an intravascular device within a blood vessel. The structure and deployment of the ring are illustrated in FIGS. 9B, 9C and 9D from that publication which are reproduced herein (with the original reference numerals) as FIGS. 1A, 1B and 1C, respectively. The entirety of the aforementioned PCT publication is hereby incorporated by reference in its entirety as if set out herein.

Referring to the features of the ring of the aforementioned PCT publication more specifically, the ring is formed from shape memory material preset to a form resembling an open pair of jaws (FIG. 1A) exhibiting a roughly circular form in plan view while having roughly a C-shaped form in side view (FIG. 1B). The ring is temporarily folded on itself and straightened for insertion into a delivery catheter. The C-shaped curvature caused the ring to assume the required alignment transverse to the catheter as it is released and opens.

This ring configuration has major advantages of compactness and simplicity of deployment. For many applications, however, a single ring does not offer sufficient stability against misalignment within a blood vessel to be a reliable platform for supporting an intravascular device. Additionally, the aforementioned publication does not discuss how devices are attached to the ring platform.

Reference is also made herein to PCT Patent Publication No. WO02/04040 which was published subsequent to the priority document of this application and which does not constitute prior art to this application. The latter publication is also hereby incorporated by reference in its entirety as if set out herein. The '040 publication discloses a particularly advantageous intravascular filter structure as shown in FIGS. 1 and 2 (reproduced here as FIGS. 2A and 2B, respectively, with the original reference numerals) including a helical outer wire and at least one axially-coextensive inner wire providing a filter configuration. In addition to various platform configurations to be discussed below, the present invention also provides various advantageous combinations of this filter structure with platforms of the present invention, and various farther modifications of the filter structure itself.

There is therefore a need for intravascular platforms which would provide enhanced stability against rotation or misalignment within a blood vessel. It would also be advantageous to provide a simple and effective form of interconnection between an intravascular device and an associated platform.

SUMMARY OF THE INVENTION

The present invention provides platforms for supporting intravascular devices, devices including such platforms, and filters suitable for use with such platforms.

The general support platform is a ring or loop structure that may be introduced into a vessel through a tailored delivery system such as a catheter. Within the catheter the ring structure is preferably collapsed into a linear form. As the ring structure is deployed within the vessel from the end of the catheter, it is designed to expand against the vessel's inner walls, and exert a certain amount of pressure in order to retain its positioning, even as the vessel may be prone to dilate elastically. The ring structure is further designed to self-align so that it adopts a profile that provides high contact with the vessel inner walls and exerts an outward pressure largely normal to the vessel walls.

The amount of acceptable vessel dilation that may be accommodated is determined by the relative dimensions of the ring and vessel the ring structure used and properties of the materials from which the ring is constructed. The mechanisms for exerting the outward pressure are a combination of the inherent springiness of the ring's material (ideally an inert memory metal), the potential to vary the thickness, cross-section and dimensions of the ring in select places, and the unfolding of the ring from its linear disposition within the delivery catheter. The size of the ring relative to the vessel may be selected to prevent the ring from fully unfolding, to tailor the outward pressure to the particular application. In practice, the ring is larger in diameter than the vessel into which it is introduced, such that the inherent springiness and constancy of stress of superelastic materials exerts an approximately constant force, even as the vessel dilates. It is believed that tip to 30% diametric dilation can be accommodated in this manner.

The ring may fabricated in linear form from a single piece of material, avoiding joining mechanisms that may compromise the material properties. The ring may also be constructed from individual pieces (wires), and only jointed at the ends or folds, to minimise the areas coming under stress, and permit joining mechanisms that do not compromise the material properties to be employed such as crimping.

The ring structure is constructed from a material with appropriate shape memory and/or superelastic properties. In particular shape memory properties enable the ring to be stored in a deformed state until used, where a state change induced by the host environment through for example change in temperature cause the ring to assume the desired shape. The shape memory allows the ring to be deployed through a tailored delivery means, where such means is designed to assume a very small profile compared to the filter's desired shape, and thereby induce a minimized stress loading on the ring's material. Similarly, superelastic properties allow gross deformation of the ring during deployment without compromising its ability to reassume the desired shape, and also permit retrieval by similar or identical means. Suitable materials with these and other suitable properties include Nitinol, which is also relatively inert in living tissue, or certain shape-memory polymers which also have an added advantage of being biodegradable, not requiring removal by operation.

The ring is put in place in the vessel by a tailored delivery system. Prior to deployment, the catheter end is positioned inside the vessel at a desired point for deployment. The ring is then pushed from the end of the catheter by suitable means, such that the portion which emerges unfolds gradually as it is no longer restrained by the catheter's walls. The folded configuration of the ring structure within the catheter is configured such that, as the ring is deployed, it adopts a transverse orientation relative to an extensional direction of the catheter, and at the same time expands to press against the vessel's inner walls.

The folded ring is designed to fit a catheter of reasonable size to the application, and to be smooth sided in order to slide freely within the catheter through potentially tortuous paths and overcome the inevitable resistance caused by its affinity to expand. An ideal cross section for the ring when folded is circular and closely matched to the catheter's inner dimensions, as this evenly distributes the expansion pressure. However, other cross-sectional designs suffice for practical application.

Various forms of folding may be used to allow the ring to be collapsed and straightened longitudinally inside a catheter. Two preferred folding configurations described hereinbelow with reference to FIGS. 9A–9G and 13A–13G, respectively. In the first preferred embodiment, each ring or loop has two diametrically opposed folds, and each ring folds in half. In the second preferred embodiment, there are four folds which are pairwise diametrically opposed, each pair being orthogonal. Those skilled in the art will appreciate that the number of folds and their arrangement may be varied widely to serve the purposes of a given application.

Thus, according to the teachings of the present invention there is provided, An intravascular platform for supporting an intravascular device, the platform comprising: (a) a first substantially closed loop of wire configured to assume a shape lying substantially on a virtual cylinder of given diameter; (b) at least one connecting wire interconnected with, and extending from, the first loop; and (c) a second substantially closed loop of wire in interconnected with the at least one connecting wire and configured to assume a shape lying substantially on the virtual cylinder at a position displaced from the first loop in a direction substantially parallel to an axis of the virtual cylinder.

According to a further feature of the present invention, the first loop, the second loop and the at least one connecting wire are temporarily deformable to assume a delivery state in which each of the loops is folded on itself and the platform is straightened to allow delivery through a minimally-invasive delivery system.

According to a further feature of the present invention, each of the first and second loops is formed from a shape-memory alloy preset to form the shape lying substantially on the virtual cylinder, each of the loops being subsequently deformed to assume the delivery state.

According to a further feature of the present invention, each of the first and second loops is implemented with a curvature configured such that advancing of the loop in a feed direction from a delivery system results in deployment of the loop in a direction generally perpendicular to the feed direction.

According to a further feature of the present invention, the first loop, the second loop and the at least one connecting wire are implemented as a unitary piece of wire.

According to a further feature of the present invention, the metal wire extends from the second loop in a direction substantially parallel to the axis and away from the first loop. The metal wire is preferably further configured to form at least part of an intravascular device, such as an intravascular filter or a stent graft.

According to a further feature of the present invention, one of the first loop and the second loop is implemented as an axially-extended loop configured such that the axially-extended loop spans a length parallel to the axis of the virtual cylinder at least equal to about 20%, and preferably 30%, of the diameter of the virtual cylinder.

According to a further feature of the present invention the axially-extended loop includes an undulating form with undulations in a direction parallel with the axis of the virtual cylinder.

According to a further feature of the present invention, the axially-extended loop includes a first undulating loop portion forming a first part of the loop, and a second undulating loop portion forming a second part of the loop, each of the first and second loop portions having an undulating form including an equal number of peaks and troughs.

According to a further feature of the present invention, the axially-extended loop includes a first undulating loop portion forming a first part of the loop, and a second undulating loop portion forming a second part of the loop, each of the first and second loop portions having an undulating form including a single peak and a single trough.

According to a further feature of the present invention, the axially-extended loop includes: (a) a plurality of ring segments together defining a substantially circular ring; and (b) at least three stabilizing projections projecting from the ring in a direction substantially parallel to the axis of the virtual cylinder.

According to a further feature of the present invention, the at least three stabilizing projections include at least two distal stabilizing projections projecting in a first direction substantially parallel to the axis and at least two proximal stabilizing projections projecting in a direction substantially opposite to the first direction.

According to a further feature of the present invention, the two distal stabilizing projections are interconnected with the ring at positions substantially evenly spaced around the ring.

According to a further feature of the present invention, the two proximal stabilizing projections are interconnected with the ring at positions substantially evenly spaced around the ring, and wherein the positions of interconnection of the proximal stabilizing projections are interspaced around the ring between positions of interconnection of the distal stabilizing projections.

According to a further feature of the present invention, the first loop and the second loop are formed from a superelastic metallic alloy.

According to a further feature of the present invention, the first loop and the second loop are formed from a shape memory metallic alloy.

According to a further feature of the present invention, the first loop and the second loop are formed from a nitinol alloy.

There is also provided according to the teachings of the present invention, an intravascular device including the aforementioned platform and further comprising an intravascular filter interconnected with the second loop, the intravascular filter including: (a) a first flexible elongated member configured to assume a substantially helical form extending for at least about one turn about the axis of the virtual cylinder; and (b) at least a second flexible elongated member connected to the first flexible elongated member at at least two spaced apart connection positions chosen such that approximately equal lengths of the first and second flexible elongated members lie between the connection positions, the second flexible elongated member being configured to assume a predefined filter form lying substantially within the substantially helical form in such a manner as to form an obstacle to passage through the substantially helical configuration, in a direction parallel to the axis, of particles having dimensions greater than a predefined value.

According to a further feature of the present invention, at least one of the first and second flexible elongated members is integrally formed with a wire forming at least part of the second loop.

According to a further feature of the present invention, the substantially helical form of the first flexible elongated member has an outer diameter smaller than the diameter of the virtual cylinder.

According to a further feature of the present invention, the substantially helical form has an outer diameter D, and wherein the predefined filter form includes a plurality of curved wire segments each curving around the axis of the virtual cylinder, wherein each of the curved wire segments passes through an inner virtual cylinder coaxial with the virtual cylinder and having a diameter D/2, a portion of each of the curved wire segments within the inner virtual cylinder undergoing an angular deflection of no more than about 60°, and preferably no more than about 40°.

According to a further feature of the present invention, the predefined filter form exhibits non-reversing curvature.

There is also provided according to a further feature of the present invention, an intravascular device including the aforementioned platform and further comprising a stent graft interconnected with the second loop.

There is also provided according to a further feature of the present invention, an intravascular device comprising: (a) a substantially closed loop of wire configured to assume a shape lying substantially on a virtual cylinder of given diameter; (b) at least one connecting wire interconnected with, and extending from, the first loop; and (c) an intravascular filter interconnected with the connecting wire, the intravascular filter including: (i) a first flexible elongated member configured to assume a substantially helical form extending for at least about one tuna about the axis of the virtual cylinder; and (ii) at least a second flexible elongated member connected to the first flexible elongated member at at least two spaced apart connection positions chosen such that approximately equal lengths of the first and second flexible elongated members lie between the connection positions, the second flexible elongated member being configured to assume a predefined filter form lying substantially within the substantially helical form in such a manner as to form an obstacle to passage through the substantially helical configuration, in a direction parallel to the axis, of particles having dimensions greater than a predefined value.

There is also provided according to a further feature of the present invention, an intravascular filter comprising: (a) a first flexible elongated member configured to assume a substantially helical form extending for at least about one turn about a central axis; and (b) at least a second flexible elongated member connected to the first flexible elongated member at at least two spaced apart connection positions chosen such that approximately equal lengths of the first and second flexible elongated members lie between the connection positions, the second flexible elongated member being configured to assume a predefined filter form lying substantially within the substantially helical form in such a manner as to form an obstacle to passage through the substantially helical configuration, in a direction parallel to the central axis, of particles having dimensions greater than a predefined value, wherein the substantially helical form lies substantially on a first virtual cylinder of a given diameter D, and wherein the predefined filter form includes a plurality of curved wire segments each curving around the central axis, wherein each of the curved wire segments passes through a second virtual cylinder coaxial with the first virtual cylinder and having a diameter D/2, a portion of each of the curved wire segments within the second virtual cylinder undergoing an angular deflection of no more than about 60°, and preferably no more than about 40°.

There is also provided according to a further feature of the present invention, an intravascular platform for supporting an intravascular device, the platform comprising a substantially closed loop of wire configured to assume a shape lying substantially on a virtual cylinder of given diameter, wherein the loop is implemented as an axially-extended loop configured such that the axially-extended loop spans a length parallel to the axis of the virtual cylinder at least equal to about 20% of the diameter of the virtual cylinder.

BRIEF DESCRIPTION OF THE DRAWINGS

The invention is herein described, by way of example only, with reference to the accompanying drawings, wherein:

FIG. 4 is a schematic side view of the platform of FIG. 3 deployed within a cut-away blood vessel;

FIG 6 is a schematic side view of an intravascular filter, constructed and operative according to the teachings of the present invention, employing an alternative platform structure of the present invention;

FIG. 7 is a schematic side view of the filter structure from the intravascular filters of FIGS. 5A–6 showing a preferred form of interconnection of the components;

FIG. 8 is a schematic plan view of a preferred filter wire configuration for use in the filter structure from the intravascular filters of FIGS. 5A–6;

FIGS. 9A–9G are a sequence of schematic views (each including a front view, a side view and a top view) showing a sequence of deployment of a distal ring from the platform of the intravascular filter of FIGS. 5A–5C within a blood vessel;

FIG. 10 is a schematic side view showing the intravascular filter of FIGS. 5A–5C fully deployed within a blood vessel;

FIG. 11 is a schematic isometric view of an alternative ring platform structure, constructed and operative according to the teachings of the present invention;

FIG. 12 is a schematic isometric view of a multiple ring platform, constructed and operative according to the teachings of the present invention, based upon the ring structure of FIG. 11;

FIGS. 13A–13G are a sequence of schematic views (each including a front view, an a top view) showing a sequence of deployment of a distal ring element from the platform of FIG. 12 within a blood vessel;

FIGS. 14A–14C are schematic front, side view and top views of a first modified ring configuration for use in a platform constricted and operative according to the teachings of the present invention;

FIGS. 15A–15C are schematic front, side view and top views of a second modified ring configuration for use in a platform constructed and operative according to the teachings of the present invention;

FIGS. 16A–16C are schematic front, side view and top views of a modified multiple-ring configuration for use in a platform constructed and operative according to the teachings of the present invention;

FIGS. 17A–17C are schematic front, side view and top views of a modified double-ring configuration for use in a platform constructed and operative according to the teachings of the present invention;

DESCRIPTION OF THE PREFERRED EMBODIMENTS

Figure 1A:
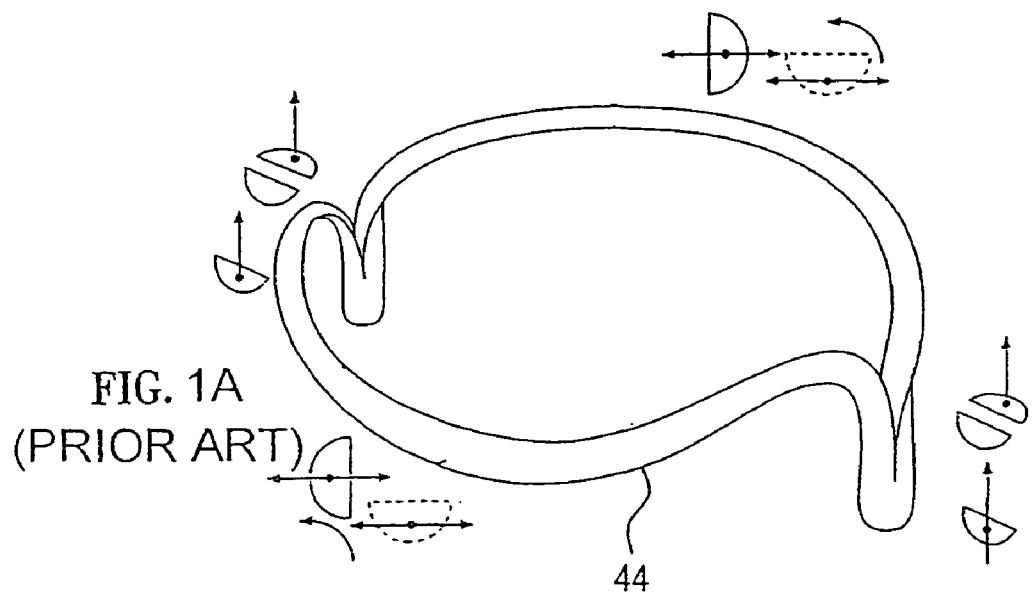
FIG. 1A is an isometric view of a ring platform according to the teachings of PCT Patent Publication No. WO01/19231, the ring being shown in a deployed state.
Figure 1B:
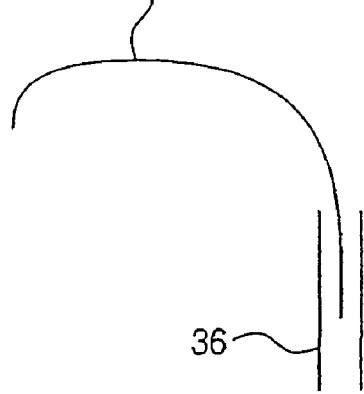
FIGS. 1B and 1C are a side view and a front view, respectively, showing the ring platform of FIG. 1A during deployment from a catheter.
Figure 1C:
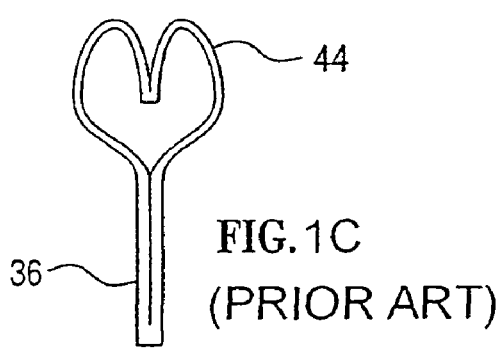

The present invention provides platforms for supporting intravascular devices, devices including such platforms, and filters suitable for use with such platforms.

The principles and operation of platforms and devices according to the present invention may be better understood with reference to the drawings and the accompanying description.

Before turning to specific features of the invention in detail, it should be appreciated that the present invention includes a number of different aspects, each of which may be used to advantage alone, and which are most preferably combined in various combinations to provide particularly advantageous devices. Specifically, a particularly preferred platform configuration, and an intravascular filter device based upon this platform, will be described herein with reference to FIGS. 3–5C and 7–10. An intravascular filter based upon a variant implementation of the platform of the present invention will be described with reference to FIG. 6. Various additional platform configurations will then be described with reference to FIGS. 11–17. Finally, with reference to FIGS. 18 and 19, applications of the platforms of the present invention to other intravascular devices will be exemplified with two preferred examples of stent graft devices.

Even within the individual implementations described herein, the devices of the present invention are believed to include numerous different aspects each of which is believed to be susceptible to patent protection individually. Thus, it should be appreciated that features of the invention indicated herein to be of particular importance should not necessarily be interpreted as necessary to all aspects of the invention, but rather according to the specific combinations of features as defined by the appended claims.

Double-Loop Platform

Referring now to the drawings, a first particularly preferred set of features of certain implementations of the present invention relates to a double ring support platform such as is exemplified by the implementations of FIGS. 3–6, 10, 12, 16A–16C, 18 and 19. In general terms, an intravascular platform constructed and operative according to the teachings of the present invention includes two substantially closed loops of wire, each configured to assume a shape lying substantially on a virtual cylinder of given diameter. The two loops are axially displaced along the cylinder and are interconnected by at least one connecting wire.

It will be immediately apparent that this double-ring configuration provides a highly advantageous combination of features. Specifically, the use of a ring element as the basis for the structure facilitates the many advantageous features of the ring platform structure described in the above-referenced PCT Patent Publication No. WO01/19231. According to the most preferred embodiments, these advantages include simple and reliable deployment by minimally invasive techniques, evenly distributed pressure around the vessel wall, and full retrievability by minimally invasive techniques. At the same time, the axially-spread double ring structure offers a high degree of stability against forces which would otherwise tend to rotate the platform out of its intended alignment within the vessel. These and other advantages of the present invention will become clearer from the following description and accompanying drawings.

It will also be apparent that the platforms of the present invention function effectively as a broadly applicable intravascular support system which can be inserted in vessels of a living being by a tailored delivery system, not involving significant surgery, arranged to be held in such a position to support other specialized devices or apparatus to carry out a prescribed function of rectifying disease or injury, or of controlling or monitoring body function by direct access to the intravascular fluid. The platform ring structure may be collapsed for introduction and removal from the body by minimally invasive means, and when deployed within the vessel conforms to the shape and structure of the vessel such that it holds its deployed position reliably and without further outside intervention. The ring thus provides a support system for other devices and apparatus. Examples of possible devices supported by the platform include, but are not limited to, one-way valves, filters and stent grafts.

The support system is preferably fully retrievable by similar tailored means, not involving significant surgery, when the rectification, monitoring or controlling procedure is terminated. A further preferred aspect of the present invention is that it ensures no significant damage to the vessel into which it is inserted by distributing frictional pressure evenly around the vessel walls. A further preferred aspect of the present invention is that it maintains position when the containing elastic vessel dilates under momentary stress conditions, thereby maintaining an even frictional pressure on the vessel walls, ensuring against displacement or revolution, due to the structure and properties of the materials from which it is constructed. A further preferred aspect of the present invention is that in one embodiment it may formed from material that has both shape memory and superelastic properties, which enable it to be introduced into a living being with a minimal profile and size of entry point, follow an arbitrarily tortuous path in that being to the required position, and recover its desired profile and properties in a fully reversible manner. A further preferred aspect of the present invention is that in several embodiments it is self-aligning, taking up optimal deployment autonomously to simplify the deployment procedure and ensure the maximum efficacy of the devices and apparatus thus supported.

It is a particularly preferred feature of the various platform embodiments of the present invention that the platform is temporarily deformable to assume a delivery state in which each loop is folded on itself and the platform is straightened to allow delivery through a minimally invasive delivery system. Most preferably, the platform and a device supported thereby are configured to be delivered through a catheter, self-deploying sequentially as released from the end of the catheter. This is most preferably achieved by forming the platform and/or device partly or wholly from a shape-memory alloy preset to form the appropriate deployed state and subsequently deformed to temporarily assume a straightened delivery state. Additionally, or alternatively, the material may be chosen to exhibit superelastic properties, thereby facilitating initial deployment within a catheter and/or retrieval into a catheter by elastic deformation of the structure. A preferred example of a suitable material for providing shape memory and superelastic properties with a selected temperature transition is the family of nickel-tin alloys known as Nitinol. The required technology for selecting compositions of Nitinol with suitable mechanical properties and temperature transitions, and for setting the shape-memory configuration, are well known in the art.

Figure 3:
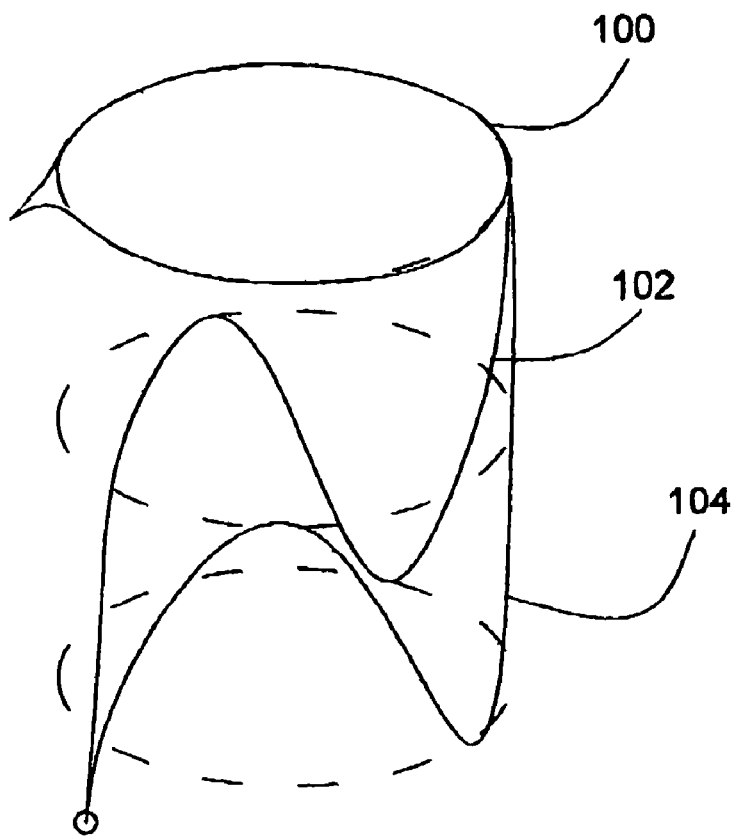
FIG. 3 is a schematic isometric view of a first preferred implementation of a platform, constricted and operative according to the teachings of the present invention, for supporting an intravascular device.

Turning now to the platform of FIGS. 3 and 4, this has a distal loop 100, a double connecting wire portion 102 and a proximal loop 104. Throughout this application, the terms "distal" and "proximal" are used in relation to the position within and order of deployment from a delivery catheter: the "distal" loop is that initially nearest the end of the catheter which is deployed first.

In this embodiment, distal loop 100 is substantially similar to the loop of PCT Patent Publication No. WO01/19231 shown in FIG. 1A, having a curvature configured such that advancing of the loop in a feed direction from a delivery system results in deployment of the loop in a direction generally perpendicular to the feed direction. This is effective to ensure correct self-alignment of the distal loop as it is released from a catheter as illustrated in the sequence of FIGS. 9A–9G.

Axially-Extended Loop

Also illustrated in the platform structure of FIGS. 3 and 4 is an additional structure for stabilizing a loop-type platform, namely, by forming the loop as an axially extended loop. It should be noted that this axially-extended loop configuration may be used either alone or in combination as part of a double loop platform structure according to the teachings of the present invention. In the case illustrated here, proximal loop 104 is implemented as an axially-extended loop configured such that it spans a length L parallel to the axis of the virtual cylinder at least equal to about 20%, and more preferably at least 30%, of the diameter of the virtual cylinder. The resulting axially-extended structure inherently has greatly enhanced stability to resist forces for rotating the ring out of its intended orientation within a blood vessel. Preferably, the axially-extended loop is used in combination with a supplementary alignment element which extends axially from the loop to provide additional stabilization, and most preferably, in combination with a second loop to provide a double-loop platform as per the aforementioned additional teachings of the present invention.

It will be noted that the "axially-extended" structure can be implemented using many different configurations. By way of non-limiting examples, a first group of implementations will be exemplified with reference to the platform structures of FIGS. 3 and 4, while a second group of implementation will be exemplified with reference to the platform structures of FIGS. 11 and 12 below. Two further examples of options will also be referred to briefly with reference to FIGS. 14A–14C and FIGS. 15A–15C, respectively.

In the implementation of axially-extended loop 104 as illustrated in FIGS. 3 and 4, the axially extension is provided by an undulating form with undulations in a direction parallel with the axis of the virtual cylinder. In other words, the loop can typically be viewed roughly as a ring modulated by a wave form with the amplitude of the wave aligned roughly parallel to the axis of the virtual cylinder resulting in a "wave" deployed around a section of the interior of the vessel wall, where the "amplitude" of the wave defines the length which the deployed ring extends along the vessel. In order to allow connection to elements proximal and distal to the ring (either integrally with an extension of the wire(s) or by other connection techniques such as by screw connections or crimping, as will be discussed below), the ring preferably features hero "tails" extending in opposite axial directions.

In the particularly preferred implementation illustrated here, deployment and retraction is rendered particularly easy by forming the ring from two undulating loop portions, each with an equal number of peaks and troughs, and most preferably as shown here, a single peak and a single trough which typically results in the distinctive "S-shape" of each half of the loop as shown. As in other examples presented herein, the two halves may be implemented as separate wires, a single loop or a single bisected strip or wire. Preferably, the axial "amplitude" from peak to trough is at least about 20% of the intended vessel diameter, and most preferably at least about 30% thereof, thereby providing excellent stability. This configuration also provides enhanced resistance to turning about its axis while spreading the retaining pressure diffusely, and readily accommodates large variations in vessel diameter.

This ring configuration has an additional advantage of providing enhanced retention when tension is applied to its "tail". Specifically, when a tail is pulled, this tends to reduce the axial extension of the wave. Since the length of the wire remains the same, this results in a tendency to increase the diameter of the ring, thereby enhancing the retention of the ring against the vessel wall.

In the preferred platform structure of FIGS. 3 and 4, the support is formed from axially-extended loop 104 together with a relatively "flat" loop 100. The two loops or rings are preferably spaced by axially extending connecting wire portion 102 so as to add a length of at least about 50% of the intended vessel diameter to the overall axial dimension of the combined support. Preferably, the entire length of the combination support platform is greater than its diameter, thereby substantially precluding rotational misalignment of the support relative to the axis of a vessel.

This structure may be used to support a range of intravascular devices by various forms of attachment, such as via screw attachment or crimping to the proximal tail of the proximal ring. In this case, the axially-extended loop typically provides the primary structural support, while the distal ring serves as an alignment anchor. In fact, in alternative implementations, the distal ring may be replaced by various other forms so long as the form used is sufficient to serve the stated function of maintaining alignment of the support within a substantially cylindrical vessel.

Platform-Filter Combinations

Figure 5C:
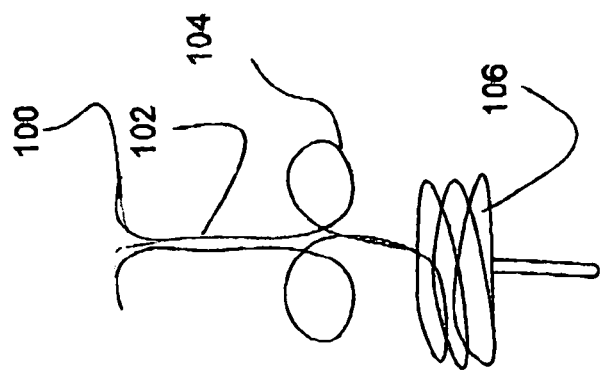
FIGS. 5A, 5B and 5C are schematic isometric, side and front views, respectively, of a preferred intravascular filter structure, constructed and operative according to the teachings of the present invention, employing the platform of FIG. 3.
Figure 5B:
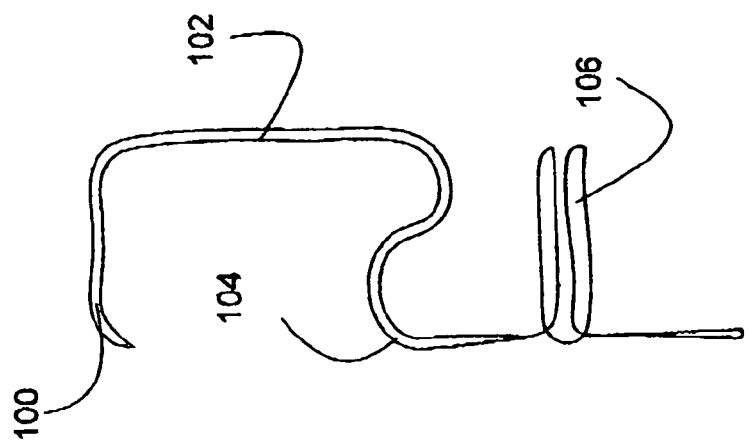
Figure 5A:
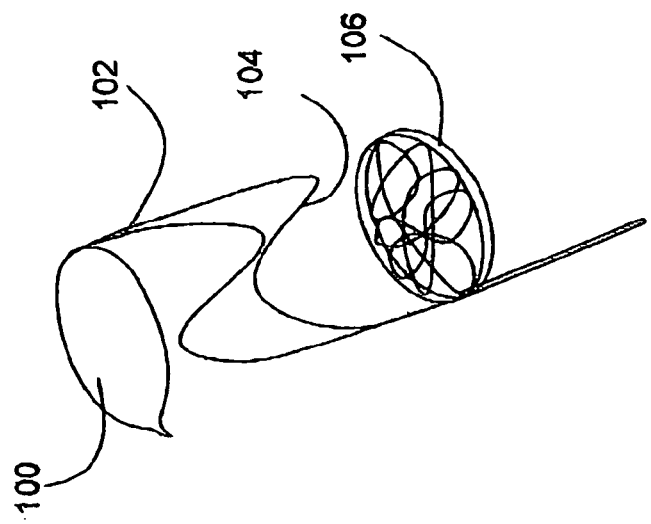

FIGS. 5A–5C illustrate a preferred intravascular filter device according to the present invention in which a platform, exemplified here by the support platform of FIGS. 3 and 4, is used to support an intravascular filter 106. Most preferably, filter 106 is of a structure essentially similar to that described in the aforementioned co-pending co-assigned PCT Patent Publication No. WO02/04040, optionally somewhat modified as will be discussed below. The filter may be of diameter equal to the support, or may be chosen to have a diameter smaller by up to about 2 mm, thereby ensuring that the majority of retention forces are borne by the support rather than the filter structure itself, and ensuring minimal radial stretching of the portion of the vessel around the filter which could reduce the effectiveness of the filter configuration. Slight undersizing of the filter relative to the support platform is also preferable for facilitating unimpeded even deployment of the filter structure. Additionally, since the platform loop structures are capable of accommodating a wider range of vessel diameters than the helical outer wire of the filter structure, slight oversizing of the platform relative to the filter allows the device to adapt through flexing of the platform loops to the full range of vessel diameters from that of the filter up to that of the platform itself.

Turning now briefly to FIG. 6, it should be noted that the double loop platforms of the present invention may also be used to advantage without either loop being individually axially extended. Thus, by way of example, FIG. 6 shows an intravascular filter device in which both loops 100 and 104 are implemented as relatively "flat" rings. Even in this case, the axial displacement between the rings defined by the connecting wire portions 102 provides an overall platform structure where the length of the platform is comparable with, and preferably larger than, the diameter of the virtual cylinder on which the loops are deployed, thereby offering highly reliable stabilization of the supported filter configuration 106.

Joining of Components

Another set of preferred features of the platforms and devices of the present invention relates to the manner in which the various wires making up the platform and device are joined. Conventional joining techniques, such as welding and soldering, are known to compromise the properties of shape-memory alloys. In order to minimize interference with the intended function of the device, various precautions are preferably taken. These include one or more of the following: reducing the total number of joints required; locating joints in low-stress (i.e., straight) regions where variations in material properties are least critical; and employing joining techniques (such as crimping) which have minimum affect on the material properties.

Referring specifically to the platforms of the present invention, the number of joints is most preferably minimized by implementing first loop 100, second loop 104 and connecting wire 102 as a unitary piece of wire. Thus, loop 100 is formed by an intermediate portion of the wire substantially closed upon itself. The adjacent two segments of the wire then continue to provide a double connecting wire 102. The two wire segments providing the connecting wire may be free parallel wires, may be twisted together, or may be secured together by one or more crimp connectors applied around them. The two wire segments then separate to form the two sides of second loop 104, typically coming together on the diametrically opposite side of the structure.

In the case of a stand-alone modular platform for use with various different intravascular devices, the free "tail" of second loop 104 terminates in a connector, such as a crown connector or threaded connector, which facilitates attachment of a range of devices thereto. Since the wires are substantially straight in the region of attachment and do not undergo significant shape transition, the properties of the structure are relatively unaffected by a joint in this region. Joining of the connector to the wires is preferably achieved by mechanical crimping or by laser micro-welding.

In the case of a platform which is permanently connected to other components to form part of an intravascular device, at least one side of the wire preferably extends beyond second loop 104, i.e., in a direction away from the first loop, typically substantially parallel to the axis, to form at least part of an intravascular device. This integral connection between the platform and the device further reduces the number of joints required, and enhances the structural integrity of the device as a whole.

Thus, in the preferred examples of FIGS. 5A–6, at least one wire segment forming the platform continues to provide one of the strands of the filter structure Optionally, both strands of the filter structure may be provided by the same unitary wire which forms the platform. In the latter case, the wire may assume one form, for example the outer helical wire, and then turn at the proximal side of the filter to provide the second form, for example the inner filter configuration. The wire then terminates at the distal side of the filter where it is preferably fastened by crimping a small Nitinol tube around the wires. Clearly, other positions for fastening the ends of the wire are also possible such as, for example, on the proximal side of the filter. In each case, a connector, such as a crown connector, is preferably associated with the wire on the proximal side of the filter for temporary connection to a guide wire or other deployment mechanism, and to facilitate retrieval of the device when no longer needed.

In a further set of examples, to be discussed further below with reference to FIGS. 18 and 19, the continuation of the wire(s) beyond second loop 104 form part of a retrievable stent graft for temporarily reinforcing a region of a vessel.

Modified Filter Configuration

Turning now to features of a preferred implementation of an intravascular filter according to the present invention, as mentioned earlier, the preferred filter structures are based upon the filters described in a co-pending co-assigned patent application published as PCT Patent Publication No. WO02/04040. In certain cases, however, a modified implementation of the filter is preferred, as will now be described with reference to FIG. 8.

Figure 2A:
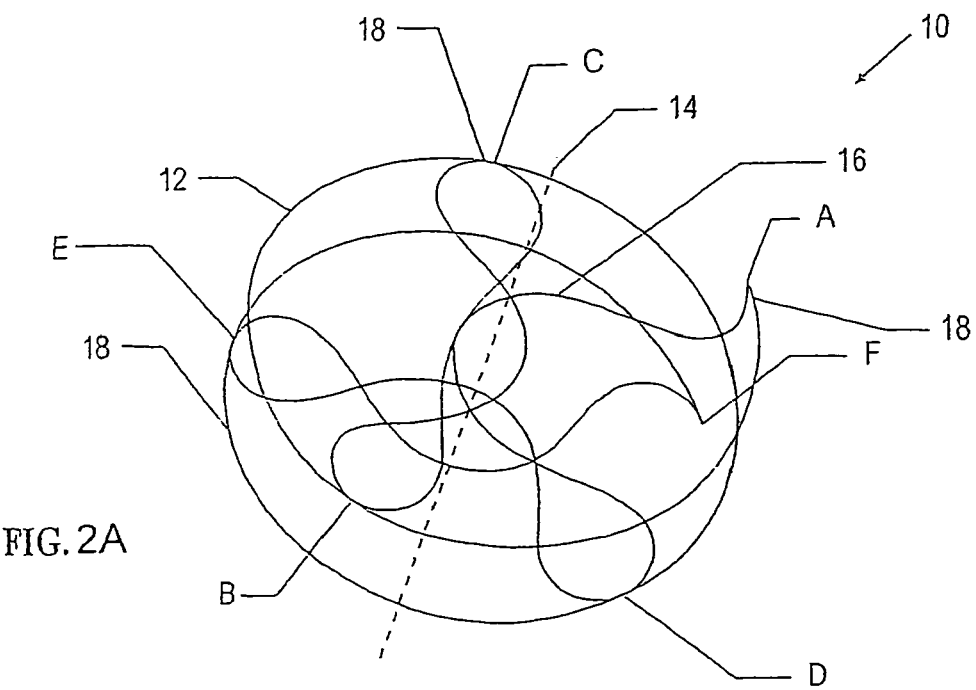
FIGS. 2A and 2B are isometric and plan views, respectively, of an intravascular filter structure corresponding to FIGS. 1 and 2 of PCT Patent Publication No. WO02/04040.
Figure 2B:
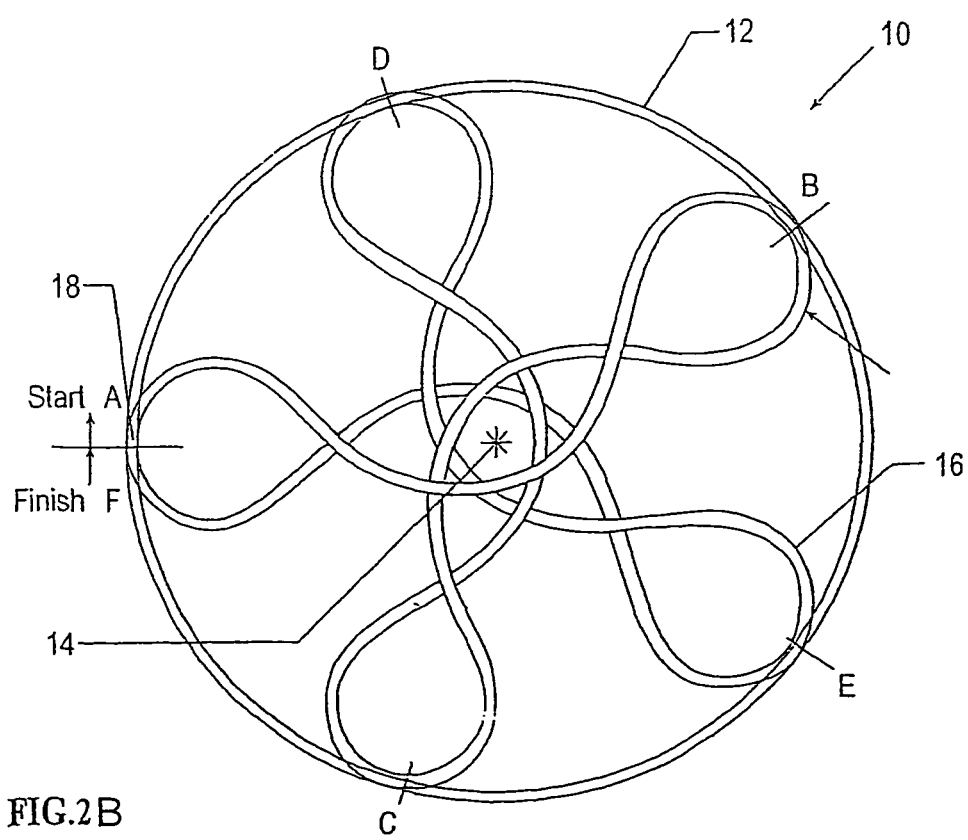

Specifically, it will be noted that the inner filter wire form of the '040 PCT publication as shown in FIGS. 2A and 2B has an intricate winding form. This form has been found effective for a range of applications, but becomes somewhat problematic for small diameter filters, as will now be explained.

During production of the inner filter wire, the required shape is typically configured initially by winding the wire on a template formed by a number of posts. For example, the form of FIG. 2B is formed using a template of one central post surrounded by five posts angularly spaced around it. The properties (composition, thickness etc.) of the wire used typically dictate a maximum permitted curvature to be used (i.e. a minimum radius of curvature) beyond which performance of the material may be degraded. In order to ensure these limits are not passed, each post is preferably formed with a radius at least equal to this minimum permitted radius of curvature.

A problem arises, however, when the diameter of the filter structure is reduced. At a certain point, it is no longer possible to maintain the preferred post size and still leave sufficient clearance to wind the wire between the posts. Instead, the thickness of the central post is reduced, raising possible problems of overstressing the portion of wire curving around the central post.

An alternative inner filter wire configuration, which offers a preferred solution to this problem, is illustrated in FIG. 8. In this case, the inner wire is formed by winding around the same six-post template with a reduce diameter central post. Unlike the form of FIG. 2B, however, the predefined filter form is here wound so as to undergo only a small deflection around the central pin, thereby avoiding the problematic extended peripheral contact between the small-diameter post and the wire.

In more precise geometrical terms, the predefined filter form here may be viewed as includes a plurality of curved wire segments 120 each curving around the axis 122 of a virtual cylinder 124 defined by the outer helical wire (not shown). Each curved wire segment 120 passes through an inner virtual cylinder 126 coaxial with virtual cylinder 124 and having a diameter D/2. A portion of each of the curved wire segments which lies within inner virtual cylinder 126 undergoes an angular deflection of no more than about 60°, and preferably no more than about 40°, so as to avoid extensive "wrapping" of the wire around the surface of the central post. This ensures that the wire does not exhibit curvature greater than its design limits even where a small central post is used.

An additional distinction between the preferred inner filter form of FIG. 8 and that of FIG. 2B is that this preferred form exhibits non-reversing curvature. In other words, as viewed in plan view along the axis, the curvature of the wire at no point switches between right-handed and left-handed as one progresses along the wire. This property also contributes to an overall reduction in the tightness of curvature of the filter form.

Alternative Ring Forms

Turning now to FIGS. 11–13G, it should be noted that the axially-extended loop platforms of the present invention may be implemented in a number of different forms. By way of an additional example, FIGS. 11–13G show an axially-extended loop formed from a plurality of ring segments 130 together defining a substantially circular ring, and at least three stabilizing projections 132, 134 projecting from the ring in a direction substantially parallel to the axis of the virtual cylinder. Preferably, the at least three stabilizing projections include at least two distal stabilizing projections 132 projecting in a first direction and at least two proximal stabilizing projections 134 projecting in a direction substantially opposite to the first direction. Distal stabilizing projections 132 and proximal stabilizing projections 134 are preferably interconnected with the ring at positions substantially evenly spaced around the ring. Most preferably, the positions of interconnection of proximal stabilizing projections 134 are interspaced around the ring between positions of interconnection of distal stabilizing projections 132.

This ring structure, referred to as a "quad-folded ring", folds to a linear state with four coextensive segments. The structure may be supplemented by a second ring or half-ring as shown in FIG. 12 and the structure can be joined by any suitable connector configuration (such as the screw connector 136 shown) to another similar structure to form an extended platform and/or to an intravascular device to be supported.

The sequence of deployment, as illustrated in FIGS. 13A–13G, has additional advantages of symmetrical deployment, resulting in a self-alignment effect. Specifically, as the linearly collapsed ring deploys from within the delivery catheter, the ring opens in two phases. In the first phase the quadrants separate pair-wise towards the vessel walls and longitudinally within the vessel, centering the delivery catheter (FIGS. 13A–13D). In the second phase, each pair of quadrant sections separate to form a roughly circular shape to maximize contact with the vessel walls and distribute pressure evenly and normal to the vessel walls (FIGS. 13E–13G). This second phase can be arranged such that the ring springs into shape from the state of FIG. 13D. An optional extension to the ring formed by a further two quadrant sections allows the ring to open gradually and softly against the vessel inner walls (FIGS. 13E–13G). This same extension may also form already means of retrieval, since it allows for a single attachment point on the ring that can exactly reverse to process of deployment as described above. The quad-folded ring does not need to reorientate, as its deployment and retrieval are appreciably longitudinal to the vessel. Furthermore, each fold alternates in its direction either with or against a given flow direction in the vessel. This guarantees that the ring deploys as close to the ideal transverse orientation as possible.

As in other embodiments of the present invention, the quad-folded ring may be constructed in a number of ways. By way of non-limiting examples, the ring may be formed from four wires crimped or welded together at the fold positions, or the ring may be constructed from a material that is split apart for example by a cutting laser. In one particular embodiment of the quad-folded ring, it is constructed from a round wire cut with two orthogonal diametrical slits to form four wires each of which is a quadrants of the overall circular cross-section. However the ring may be equally constructed from wires of any cross-sectional shape such as elliptical, circular, for the purposes of a particular application or for desirable deployment properties.

In alternative implementations, the quad-folded ring is formed from four identical pieces of quadrant cross-sectional wire suitably curved and welded or crimped at either end in a pair wise manner, where the pairing is adjacent and rotated 90 degrees at opposite ends. The joints are flat face to flat face. Inside the catheter the straightened pieces meet fully along the length of their flat faces to form a cylinder. Outside the catheter, the four pieces curve away from one another increasingly towards their centers, to assume a circular shape when viewed along the vessel. The optional extension is preferably formed by extending an adjacent pair of wires, forming a further fold point that can also be used for attachment of a pulling device for retrieval.

In yet a further implementation, the quad-folded ring may be constructed from one closed annular piece of wire, preferably of quadrant cross-section, as illustrated in FIG. 11. In this case the folds when inside the catheter are formed in a similar way to a hair grip, allowing a very small minimum radius to be achieved by suitable variation in thickness and preparation of the material, such that it does not suffer fatigue.

Referring now briefly to FIGS. 14A–17C, these illustrate a number of additional modifications to a ring structure which may be used alone, or in combination with other features of the present invention, to offer enhanced stability of a ring platform.

Specifically, in the modified ring form of FIGS. 14A–14C, waves are put into the wires of the two halves of the ring which are of sufficient amplitude to achieve the desired rotational prevention for the whole structure. Preferably, in a manner analogous to the S-shape loop described above, each half of the loop is formed with a full cycle waveform (see FIG. 14B), most preferably in antiphase between the wires.

In the modified form of FIGS. 15A–15C, the wire is split to provide opposing axial amplitude waves in a single segment of wire. This provides a smooth transformation, rotational stability and advantages of improved retention.

FIGS. 16A–16C illustrate an alternative multi-ring platform implementation in which a number of bifolded rings are attached together such that, when deployed, they are axially spaced along the length of the vessel by a fixed amount. In one form, only one fold of each ring is joined (see FIG. 16B). Two or possibly more bifolded rings can be joined in this manner and pushed out of a catheter as a single unit of four or more wires respectively. The rings are only joined at one side (the pushing side of deployment) to allow them to be of different length in linear form, accommodating the desired displacement in deployed form.

In a final variant of this form illustrated in FIGS. 17A–17C, two bifolded rings are joined at both folds on each side. In linear form all the wires are of the same length, but the anti-rotational property is achieved by curving the wires; one ring curves opposite to the second ring, accommodating the desired displacement.

Stent Graft Applications

As mentioned earlier, the platforms of the present invention are applicable to a wide range of applications in which an intravascular device is deployed in a blood vessel. By way of an additional non-limiting example, FIGS. 18 and 19 illustrate retrievable stent graft structures based upon the support platforms of the present invention.

Figure 18:
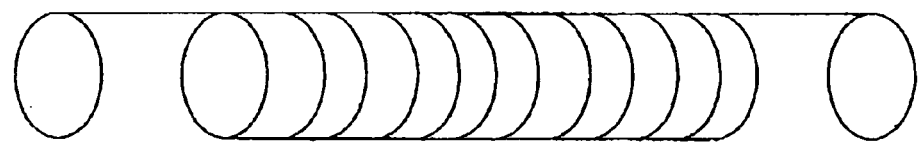
FIG. 18 is a schematic isometric view of a cylindrical stent graft supported by a number of platforms constructed and operative according to the teachings of the present invention.

Thus, FIG. 18 shows a stent graft in which a cylindrical sleeve of suitable impermeable material, as is known in the art, is supported by one or more ring-based platform. The cylindrical sleeve may be unsupported except at its ends, with the ring-based platforms serving to anchor the device and facilitate retrieval. Alternatively, the sleeve may have a supporting structure such as a number of support rings or ribs spaced along the length of the graft, or a helical support wire extending between the support platforms.

Figure 19:
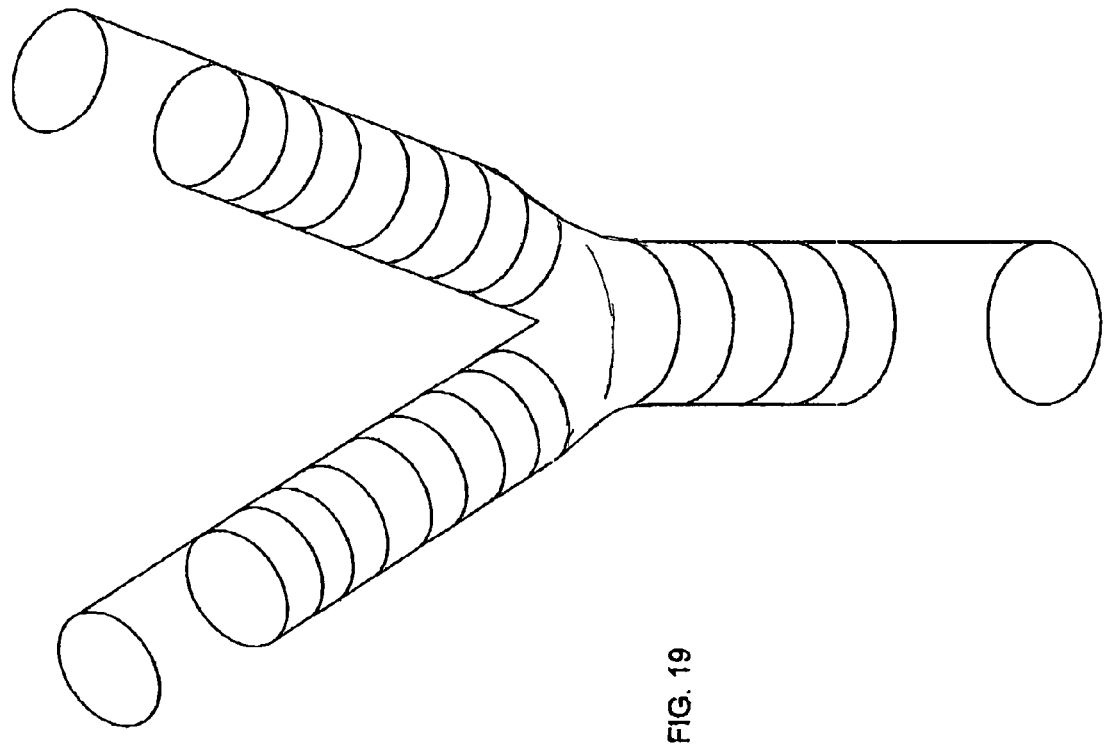
FIG. 19 is a schematic isometric view of a bifurcated stent graft supported by a number of platforms constructed and operative according to the teachings of the present invention.

FIG. 19 shows a similar stent graft implementation for application at a bifurcation of a vessel. This allows reinforcement of the vessel in the region of the bifurcation, with each open end of the graft supported by a platform of appropriate dimensions, implemented according to the teachings of the present invention.

It will be readily apparent that the resulting stent graft structure provides profound advantages compared to the non-retrievable balloon-based or self-expanding stent graft structures commonly in use. Specifically, the structure allows use of a small delivery system, limited only by the "folded size" of the synthetic tube of the graft, is easy to position with a simple "push-release" from a delivery system, and provides full retrievability for repositioning or removal when surgery is performed.

It should be noted that various additional variations of the implementations described herein are also believed to be of particular significance. For example, it may be preferably to implement different parts of a platform and filter combination, or other associated devices, with different materials having differing mechanical or other properties. Furthermore, a device may be combined with platform loops in any desired sequence, with single or multiple platform loops at one or both ends of a device and/or interspaced at intermediate regions of a device.

Finally, although described above in the form of a double-wire filter structure, it should be noted that the use of the platforms of the present invention as a support structure allow implementation of an intravascular filter using a filter wire form such as that of the inner wire of FIG. 2A or 8 without any additional helical outer wire.

It will be appreciated that the above descriptions are intended only to serve as examples, and that many other embodiments are possible within the scope of the present invention as defined by the appended claims.

What is claimed is:

1. An intravascular platform supporting an intravascular device, the platform comprising:
  (a) a first closed loop of wire configured to assume a shape lying substantially on a virtual cylinder of given diameter;
  (b) at least one connecting wire interconnected with, and extending from, said first loop;
  (c) a second closed loop of wire interconnected with said at least one connecting wire and configured to assume a shape lying substantially on the virtual cylinder at a position displaced from said first loop in a direction substantially parallel to an axis of the virtual cylinder; and
  (d) an intravascular filter interconnected to said second loop and deployed primarily on a side of said second loop away from said first loop, said intravascular filter being supported by said second loop, wherein said intravascular filter includes:
    (i) a first flexible elongated member configured to assume a substantially helical form extending for at least about one turn about the axis of said virtual cylinder, and
    (ii) at least a second flexible elongated member connected to said first flexible elongated member at at least two spaced apart connection positions chosen such that approximately equal lengths of said first and second flexible elongated members lie between said connection positions, said second flexible elongated member being configured to assume a predefined filter form lying substantially within said substantially helical form in such a manner as to form an obstacle to passage through said substantially helical configuration, in a direction parallel to said axis, of particles having dimensions greater than a predefined value.

2. The platform of claim 1, wherein said first loop, said second loop and said at least one connecting wire are temporarily deformable to assume a delivery state in which each of said loops is folded on itself and the platform is straightened to allow delivery through a minimally invasive delivery system.

3. The platform of claim 1, wherein said first loop, said second loop and said at least one connecting wire are implemented as a unitary piece of wire.

4. The platform of claim 1, wherein at least one of said first loop and said second loop is implemented as an axially-extended loop configured such that said axially-extended loop spans a length parallel to the axis of the virtual cylinder at least equal to about 20% of the diameter of said virtual cylinder.

5. The platform of claim 4, wherein said axially-extended loop includes an undulating form with undulations in a direction parallel with the axis of the virtual cylinder.

6. The platform of claim 4, wherein said axially-extended loop includes a first undulating loop portion forming a first part of said loop, and a second undulating loop portion forming a second part of said loop, each of said first and second loop portions having an undulating form including an equal number of peaks and troughs.

7. The platform of claim 4, wherein said axially-extended loop includes a first undulating loop portion forming a first part of said loop, and a second undulating loop portion forming a second part of said loop, each of said first and second loop portions having an undulating form including a single peak and a single trough.

8. The platform of claim 4, wherein said axially-extended loop includes:
   (a) a plurality of ring segments together defining a substantially circular ring; and
   (b) at least three stabilizing projections projecting from said ring in a direction substantially parallel to the axis of the virtual cylinder.

9. The platform of claim 8, wherein said at least three stabilizing projections include at least two distal stabilizing projections projecting in a first direction substantially parallel to the axis and at least two proximal stabilizing projections projecting in a direction substantially opposite to said first direction.

10. The platform of claim 9, wherein said two distal stabilizing projections are interconnected with said ring at positions substantially evenly spaced around said ring.

11. The platform of claim 10, wherein said two proximal stabilizing projections are interconnected with said ring at positions substantially evenly spaced around said ring, and wherein said positions of interconnection of said proximal stabilizing projections are interspaced around said ring between positions of interconnection of said distal stabilizing projections.

12. The platform of claim 1, wherein at least one of said first and second flexible elongated members is integrally formed with a wire forming at least part of said second loop.

13. The platform of claim 1, wherein said intravascular filter has an outer diameter smaller than the diameter of said virtual cylinder.

14. The platform of claim 1, wherein said predefined filter form is a lobed form exhibiting non-reversing curvature.

15. The platform of claim 1, further comprising a connector configured for interconnecting said intravascular filter with said second loop.

16. An intravascular device comprising:
   (a) a substantially closed loop of wire configured to assume a shape lying substantially on a virtual cylinder of given diameter;
   (b) at least one connecting wire interconnected with, and extending from, said first loop; and
   (c) an intravascular filter interconnected with said connecting wire, said intravascular filter including:
      (i) a first flexible elongated member configured to assume a substantially helical form extending for at least about one turn about the axis of said virtual cylinder; and
      (ii) at least a second flexible elongated member connected to said first flexible elongated member at at least two spaced apart connection positions chosen such that approximately equal lengths of said first and second flexible elongated members lie between said connection positions, said second flexible elongated member being configured to assume a predefined filter form lying substantially within said substantially helical form in such a manner as to form an obstacle to passage through said substantially helical configuration, in a direction parallel to said axis, of particles having dimensions greater than a predefined value.

17. The intravascular device of claim 16, wherein at least one of said first and second flexible elongated members is integrally formed with a wire forming at least part of said loop.

18. The intravascular device of claim 16, wherein said substantially helical form of said first flexible elongated member has an outer diameter smaller than the diameter of said virtual cylinder.

19. The intravascular filter of claim 16, wherein said predefined filter form exhibits non-reversing curvature.

20. An intravascular system comprising:
   (a) a first platform including:
      (i) a first closed loop of wire configured to assume a shape lying substantially on a virtual cylinder of given diameter,
      (ii) at least one connecting wire interconnected with, and extending from, said first loop, and
      (iii) a second closed loop of wire interconnected with said at least one connecting wire and configured to assume a shape lying substantially on the virtual cylinder at a position displaced from said first loop in a direction substantially parallel to an axis of the virtual cylinder:
   (b) a second platform including:
      (i) a first closed loop of wire configured to assume a shape lying substantially on a virtual cylinder of given diameter,
      (ii) at least one connecting wire interconnected with, and extending from, said first loop, and
      (iii) a second closed loop of wire interconnected with said at least one connecting wire and configured to assume a shape lying substantially on the virtual cylinder at a position displaced from said first loop in a direction substantially parallel to an axis of the virtual cylinder; and
   (c) an intravascular device interconnected with, and supported between, said first and second platforms.

* * * * *